US006648851B2

(12) United States Patent
Pyret et al.

(10) Patent No.: US 6,648,851 B2
(45) Date of Patent: Nov. 18, 2003

(54) APPLICATOR HAVING PARTIAL INSERTION CANNULA

(75) Inventors: Thomas Walter Pyret, Portage, MI (US); Fred W. Wall, Otsego, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/091,376

(22) Filed: Mar. 5, 2002

(65) Prior Publication Data

US 2002/0133138 A1 Sep. 19, 2002

Related U.S. Application Data

(60) Provisional application No. 60/273,767, filed on Mar. 6, 2001.

(51) Int. Cl.[7] .................................................. A61M 1/06

(52) U.S. Cl. .......................................... 604/73; 604/506

(58) Field of Search ....................... 604/506, 73, 93.01, 604/117, 162, 167.06, 170.01, 181, 182, 186, 192, 197, 198, 218, 239, 263, 264, 272; 128/919

(56) References Cited

U.S. PATENT DOCUMENTS

| | | | | |
|---|---|---|---|---|
| 3,434,473 A | | 3/1969 | Smith | |
| 4,022,191 A | | 5/1977 | Jamshidi | |
| 4,850,970 A | | 7/1989 | Sutherland | |
| 4,981,472 A | * | 1/1991 | Ennis et al. | 604/117 |
| 5,053,020 A | | 10/1991 | Manchester | |
| 5,059,172 A | | 10/1991 | Sutherland et al. | |
| 5,489,266 A | * | 2/1996 | Grimard | 604/191 |

FOREIGN PATENT DOCUMENTS

WO WO 84/03840 10/1984

OTHER PUBLICATIONS

R. L. Boddie & S. C. Nickerson, *Dry Cow Therapy: Effects of Method of Drug Administration on Occurrence of Intramammary Infection*, Journal of Dairy Science vol. 69, No. 1, 1986, pp. 253–257.

* cited by examiner

*Primary Examiner*—Manuel Mendez
(74) *Attorney, Agent, or Firm*—Flynn, Thiel, Boutell & Tanis, P.C.

(57) ABSTRACT

An applicator for administering a medication to an animal, particularly a mastitis treatment, is made up of an elongated syringe having an integral blunt-tipped cannula provided at one end thereof. The cannula has a first portion for partial insertion of the cannula and a second portion for complete insertion of the cannula. The diameter of the cannula first portion is smaller than the diameter of the cannula second portion and the cannula first and second portions join at an annular shoulder which limits the partial insertion of the cannula.

10 Claims, 1 Drawing Sheet

APPLICATOR HAVING PARTIAL INSERTION CANNULA

This application claims the benefit of provisional application Ser. No. 60/273,767 filed Mar. 6, 2001.

FIELD OF THE INVENTION

The present invention relates to applicators which are used for medical purposes such as administering a medication to an animal for mastitis and, more particularly, to an applicator having a partial insertion cannula for limiting the depth of the insertion of the cannula during the administration of the medication.

BACKGROUND OF THE INVENTION

Bovine mastitis is a problem which afflicts a large number of dairy cows. This mastitis is an inflammation of the cow's mammary gland and has a detrimental effect on milk production and profitability of a farm dairy operation. Treatment of bovine mastitis has typically been accomplished by administering various antibiotic compositions into an animal's udder through a teat canal.

Initially, mastitis infusion syringes were provided from the antibiotic supplier as a molded plastic, disposable unit having a single piece plastic cover which typically snap-fitted onto the hub of the syringe at the base of the cannula to cover the cannula prior to use. The protective cap was removed at the time of treatment from the cannula and the cannula end inserted into the cow's teat end, passed up through the teat canal and positioned within a teat cistern. After being correctly positioned, the treatment antibiotic is injected from the syringe directly into the cow's teat cistern.

Studies have shown that full cannula insertion through the teat canal can have detrimental effects on the effectiveness of the mastitis treatment. Research has shown that in some instances, bacteria infecting the keratin lining of the teat canal can be carried into the teat cistern by the mastitis cannula during the full insertion thereof to produce mastitis.

A cow's teat canal is approximately 5 to 10 mm in length and has a very narrow lumen of about 0.4 to 1.63 mm. This narrow canal helps prevent bacteria from entering a cow's udder. Although some bacteria may survive in the keratin lining and secretions in the distal teat canal, they are prevented by the healthy teat canal from traveling the full length of the canal. During full cannula insertion, these bacteria can be aided in their travel of the teat canal by the cannula. It has also been discovered that the teat canal or duct keratin layer, which helps control bacterial penetration into the udder, may be damaged by full cannula insertion. Full cannula insertion also may cause the full length of the teat canal lumen to dilate and allow increased bacterial travel and penetration into the teat cistern and mammary gland.

In order to avoid the above problems, a partial insertion technique has been developed wherein the mastitis cannula is inserted into the teat end of the teat canal only to a depth of generally about 3–4 mm. Although this technique is beneficial in the treatment of mastitis, it has made the treatment procedures more difficult and time consuming for the dairyman out in the field. This technique requires that the cannula insertion depth be limited to generally about 3–4 mm to avoid teat canal keratin damage, dilating of the entire teat canal and preventing the transport of bacteria from the distal teat canal into the teat cistern. In order to fulfill this need, Ennis, III et al, U.S. Design Pat. No. Des 308,724, discloses a short mastitis cannula.

Ennis, III et al, U.S. Pat. No. 4,981,472, also discloses a cannula assembly for injecting medicinal fluid into an animal's teat comprising a first tapered cannula. Second and third cannulas can be provided to provide the user with a choice of cannulas of three different lengths for insertion into a teat.

Manchester, U.S. Pat. No. 5,053,020, discloses an applicator for administering medication comprising a syringe cylinder having a first reduced diameter, blunt-tipped cannula integral with and projecting therefrom. A second cannula of reduced diameter and also having a blunt tip is detachably mounted on the base of the first cannula to offer the user a choice between partial and full insertion of the cannula.

Sutherland, U.S. Pat. No. 5,059,172, discloses a syringe with a two part mastitis cannula cap comprising an outer cap and an inner cap. The inner cap is not as long as the cannula so that a free end of the cannula can protrude beyond an end face of the inner cap. Controlled depth partial insertion of the cannula into the teat canal of a dairy cow can be accomplished by removal of only the outer cap. Alternatively, full depth cannula insertion can be accomplished by removing both parts of the cap.

Although the above patents provide methods for partial and full insertion of a cannula, they require manual manipulation of cannulas or caps provided on the cannulas in order to afford the desired administration technique. This increases the risk of contamination and makes the administration of the medication unnecessarily complicated. As such, there is a need for a mastitis treatment applicator which can administer a medication by either partial or full insertion which minimizes the risk of contamination and does not require extensive physical manipulation.

SUMMARY OF THE INVENTION

According to the invention, there is provided a method of using an applicator for administering a medication in which the applicator comprises an elongated syringe having an integral blunt-tipped cannula extending longitudinally from an end thereof. The cannula has a longitudinally extending bore and comprises a first portion for partial insertion of the cannula and a second portion for complete insertion of the cannula with an annular ridge provided between the cannula first portion and cannula second portion for limiting the partial insertion of the cannula. A detachable protective cap can be provided over the cannula to protect the contents of the syringe from contamination and sealing the cannula against leakage. The annular ridge serves as an indicator for the insertion depth of the cannula in order to obtain partial insertion. If it is desired to have full insertion, the diameter of the cannula is sufficiently small so that the cannula second portion can be completely inserted into the teat canal of an animal.

DESCRIPTION OF THE PREFERRED EMBODIMENTS

Figure 2:
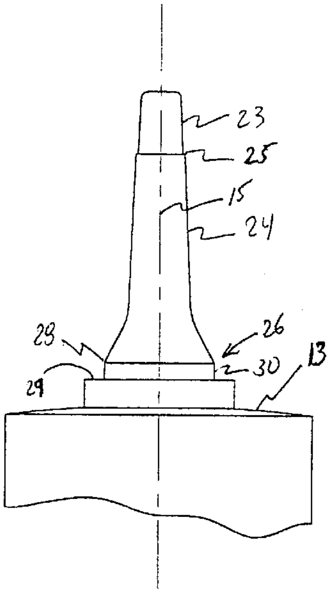
FIG. 2 is an enlarged view of the cannula of FIG. 1.
Figure 1:
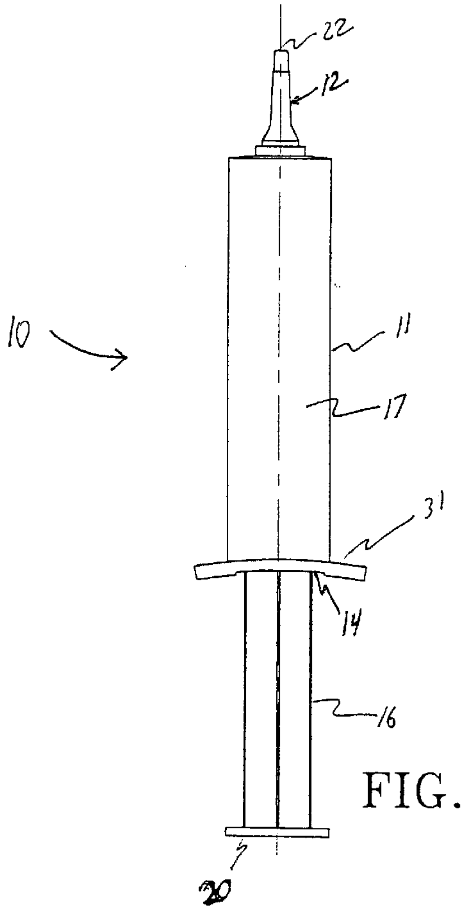
FIG. 1 is an elevation view of an applicator according to the present invention.
Figure 3:
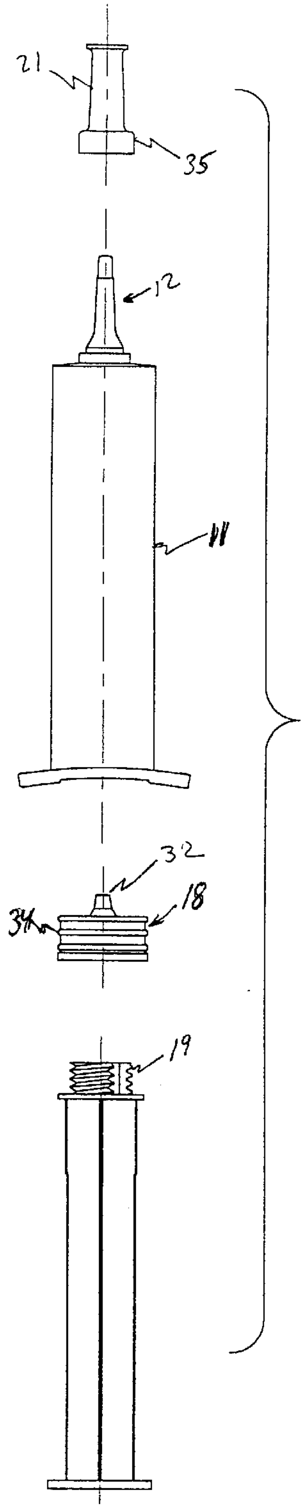
FIG. 3 is an exploded view of the applicator of the present invention.

With reference to the drawings, like reference characters designate corresponding parts in FIGS. 1–3.

Referring to FIGS. 1–3, an applicator 10 is shown comprising an elongated syringe body 11 having a closed end 13 and an open end 14. Cannula 12 is provided on the syringe body closed end and has a bore 15 extending longitudinally therethrough which is coaxial and communicates with a chamber 17 provided in the syringe body 11. The syringe body 11 and cannula 12 are of integral construction and preferably molded from a thermoplastic material such as polypropylene or polyethylene.

The cannula 12 is joined to the syringe body closed end 13 by a hub portion 26 having an upper flat wall portion 29. The cannula 12 extends longitudinally away from the flat wall portion 29 and terminates at a blunt tip 22. The cannula 12 comprises a first portion 23 joined to a second portion 24 at an annular ridge 25. The cannula first portion 23 extends from the cannula blunt tip 22 to the annular ridge 25 and the cannula second portion 24 extends from the annular ridge 25 to the flat wall portion 29. The end of the cannula first portion 23 directly adjacent to the annular ridge 25 has a smaller diameter than the end of the cannula second portion 24 directly adjacent to the annular ridge 25 and the difference in the diameters between the cannula first portion 23 and the cannula second portion 24 form the annular ridge 25. An annular rib 28 and a groove 30 are formed in the cannula second portion 24 and cooperate with a cap 21 having a flange 35 to secure the cap 21 on the cannula 12.

In practice, the ridge 25 is abutted against the entrance of the teat of the animal so that the first portion 23 is positioned inside of the teat canal for partial insertion administration. The cannula second portion 24 is also of acceptable diameter to be completely inserted into the teat canal of the animal if it is desired to have full insertion administration of a medication.

In the illustrated embodiment, a plunger rod 16 is provided which has a threaded end 19 and a thumb engaging member 20 provided on an opposite end thereof. An elastically deformable plunger stopper 18 is threadedly engaged with the plunger threaded end 19 and secured thereon. A protuberance 32 is provided on a top surface of the plunger stopper 18 and helps discharge a medication out of the cannula 12. The plunger stopper 18 has a diameter 34 which is slightly larger than the internal diameter of the syringe body chamber 17 so that when the plunger stopper 18 is inserted into the syringe body 17, it effects a sealing thereof. The plunger rod 16 and plunger stopper 18 are received in the syringe body open end 14 to confine a medication in the chamber 17. A finger gripping flange is provided at the syringe body open end 14 and is used to help stabilize the applicator when the thumb of the user is engaged with the thumb engaging member 20 for administration of the medication through the cannula 12. If desired, the thread end 19 and the elastically deformable plunger stopper 18 can be omitted and a conventional plunger rod end (not illustrated) used.

The detachable cap 21 has an annular flange 35 which is adapted to engage with the annular rib 28 and groove 30 to seal the contents of the syringe and protect the cannula from damage and contamination during storage, shipment and use.

Although a particular preferred embodiment has been described and illustrated, the present invention contemplates such changes as lying within the scope of the appended claims.

What is claimed is:

1. An applicator for administering a medication, comprising an elongated syringe having an integral blunt-tipped cannula extending longitudinally from an end thereof, said cannula having a longitudinally extending bore and comprising a first portion for partial insertion of the cannula and a second portion for complete insertion of the cannula, said cannula first portion extending longitudinally from the blunt tip of the cannula to the cannula second portion, an end of the cannula second portion adjacent an end of the cannula first portion having a larger outside diameter than the outside diameter of the cannula first portion adjacent end and forming an annular shoulder between the cannula first portion and cannula second portion for limiting the partial insertion of the cannula.

2. The applicator of claim 1, wherein said syringe additionally comprises a barrel portion and a plunger portion, said barrel portion defining an injection chamber for receiving said plunger portion therein and comprising a cylindrical body having a hub portion provided at one end thereof and an opposite open end through which said plunger portion is received.

3. The applicator of claim 2, wherein the cannula extends from the hub portion and the hub portion comprises a flat wall portion, an annular rib and a circumferentially extending groove provided between the annular rib and the flat wall portion.

4. The applicator of claim 2, wherein the plunger comprises an elongated body having threads provided at one end thereof, a thumb engaging member provided at the opposite end thereof and a deformable stopper threadedly engaged with the one end of the elongated body.

5. The applicator of claim 2, additionally comprising a cap having an annular flange member for sealingly engaging with the hub portion.

6. The applicator of claim 4, wherein a protuberance is provided on a top surface of the deformable stopper which is coaxial with the longitudinally extending bore.

7. A method of administering a medication to a teat of an animal's udder comprising the steps of providing an applicator comprising an elongated syringe having an integral blunt-tipped cannula extending longitudinally from an end thereof, said cannula having a longitudinally extending bore and comprising a first portion for partial insertion of the cannula and a second portion for complete insertion of the cannula, said cannula first portion extending longitudinally from the blunt tip of the cannula to the cannula second portion, an end of the cannula second portion adjacent an end of the cannula first portion having a larger outside diameter of the cannula first portion adjacent end and forming an annular shoulder between the cannula first portion and cannula second portion for limiting the partial insertion of the cannula;

inserting the cannula into the teat of the animal; and administering a medication from the cannula into the teat of the animal.

8. The method of claim 7, wherein the cannula is inserted into the teat to a depth where the annular shoulder abuts against the entrance of the teat.

9. The method of claim 7, wherein the cannula is inserted into the teat to a depth where the annular shoulder is contained within the teat.

10. An applicator for administering a medication comprising an elongated syringe having an injection chamber for receiving a plunger portion, the syringe also having a hub portion at one end and an opposite open end through which said plunger portion is received, the syringe further having a cannula second portion that extends from the hub portion to an annular shoulder, a cannula first portion having a diameter that is smaller than the cannula second portion at the annular shoulder, the cannula first portion extending from the annular shoulder and terminating in a blunt tip, and a bore extending longitudinally through the second and first portions of the cannula, the bore being coaxial and communicating with the chamber, the annular shoulder being substantially perpendicular to the bore.

* * * * *